(12) United States Patent
Pianca et al.

(10) Patent No.: US 7,343,205 B1
(45) Date of Patent: Mar. 11, 2008

(54) SYSTEM AND METHOD FOR INSERTION OF A DEVICE INTO THE BRAIN

(75) Inventors: Anne M Pianca, Valencia, CA (US); Janusz A Kuzma, Parker, CO (US)

(73) Assignee: Boston Scientific Neuromodulation Corp., Valencia, CA (US)

(*) Notice: Subject to any disclaimer, the term of this patent is extended or adjusted under 35 U.S.C. 154(b) by 365 days.

(21) Appl. No.: 10/642,851

(22) Filed: Aug. 18, 2003

Related U.S. Application Data

(60) Provisional application No. 60/404,692, filed on Aug. 20, 2002.

(51) Int. Cl.
*A61N 1/18* (2006.01)

(52) U.S. Cl. ............... 607/116; 607/45; 604/174

(58) Field of Classification Search ............ 607/116, 607/45; 604/174, 175; 600/378
See application file for complete search history.

(56) References Cited

U.S. PATENT DOCUMENTS

| | | | |
|---|---|---|---|
| 4,350,159 A | | 9/1982 | Gouda |
| 4,931,056 A | | 6/1990 | Ghajar et al. |
| 4,955,891 A | | 9/1990 | Carol et al. |
| 5,116,345 A | | 5/1992 | Jewell et al. |
| 5,300,080 A | | 4/1994 | Clayman et al. |
| 5,330,485 A | | 7/1994 | Clayman et al. |
| 5,390,671 A | * | 2/1995 | Lord et al. ............... 600/347 |
| 5,713,858 A | * | 2/1998 | Heruth et al. ........ 604/288.02 |
| 5,752,937 A | | 5/1998 | Otten et al. |
| 5,927,277 A | * | 7/1999 | Baudino et al. .......... 600/386 |
| 6,011,996 A | * | 1/2000 | Gielen et al. ............. 600/378 |
| 6,261,300 B1 | | 7/2001 | Carol et al. |
| 6,301,492 B1 | * | 10/2001 | Zonenshayn ............. 600/378 |
| 6,413,263 B1 | * | 7/2002 | Lobdill et al. ........... 606/129 |
| 6,416,520 B1 | | 7/2002 | Kynast et al. |
| 6,456,889 B2 | | 9/2002 | Pianca et al. |
| 6,527,782 B2 | * | 3/2003 | Hogg et al. .............. 606/130 |
| 2001/0027336 A1 | | 10/2001 | Gielen et al. |
| 2002/0143376 A1 | * | 10/2002 | Chinn et al. ............. 607/115 |
| 2005/0021104 A1 | * | 1/2005 | DiLorenzo ................ 607/45 |

OTHER PUBLICATIONS

Merriam-Webster Online Dictionary, (http://www.webster.com); searched: offset.*
Merriam-Webster Online Dictionary, (http://www.webster.com); searched: stereotactic(stereotaxic).*
"System and Method for Selective Multi-site Microelectrode Recording", IP.com, IPCOM000016587D, Jul. 1, 2003.
"Universal Instrument Guide and Surgical Insertion Tool for Stereotactic Frames", IP.com, IPCOM000011023D, Feb. 7, 2003.

(Continued)

*Primary Examiner*—Angela D. Sykes
*Assistant Examiner*—Alyssa M. Alter
(74) *Attorney, Agent, or Firm*—Travis K. Laird; AdvantEdge Law Group, LLC

(57) ABSTRACT

A deep brain stimulation lead system has a medical lead, or similar elongate medical insertion device, securable with a lead lock through a cannula slit, thereby allowing a lead to remain electrically operative and preventing movement of the lead during removal of a stylet, recording microelectrode, or cannula.

20 Claims, 6 Drawing Sheets

OTHER PUBLICATIONS

Pianca, et al. Inventors for AB-164U; U.S. Appl. No. 10/035,745; filed Dec. 28, 2001; entitled "Systems and Methods of Implanting a Lead for Brain Stimulation".

Pianca inventor for AB-266U; U.S. Appl. No. 10/459,068; filed Jun. 11, 2003; entitled "System for Permanent Electrode Placement Utilizing Microelectrode Recording Methods".

* cited by examiner

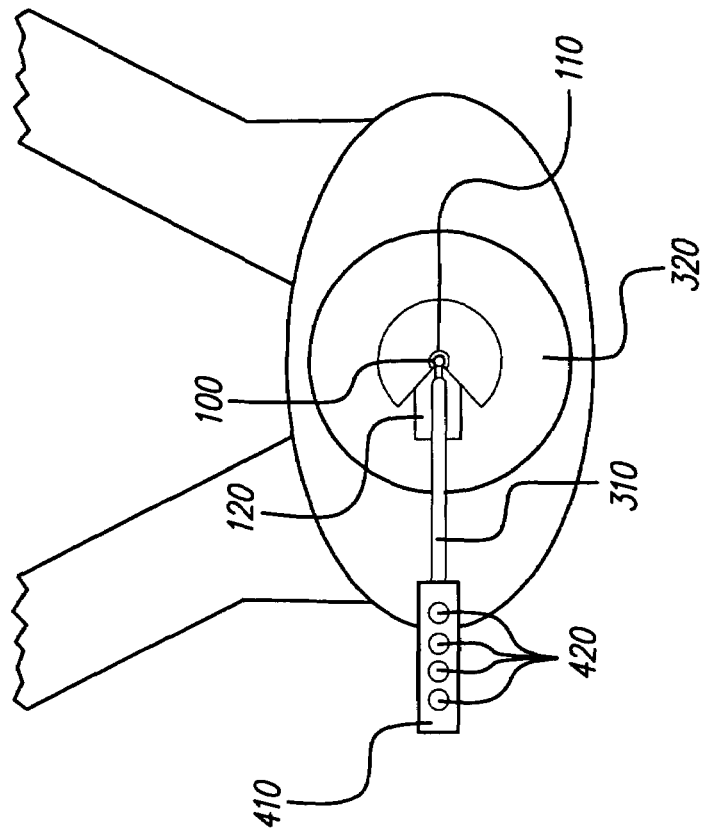
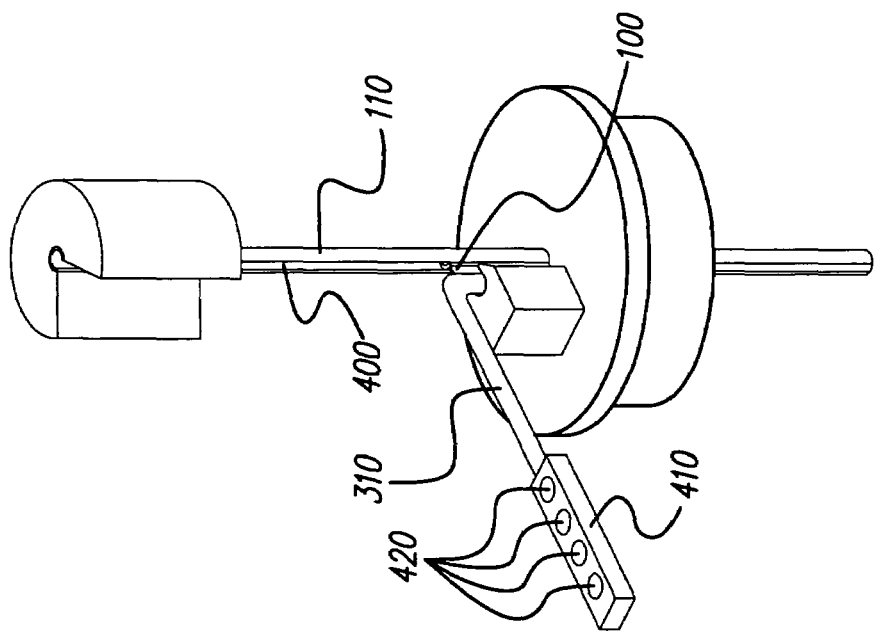

SYSTEM AND METHOD FOR INSERTION OF A DEVICE INTO THE BRAIN

The present application claims the benefit of U.S. Provisional Patent Application Ser. No. 60/404,692, filed Aug. 20, 2002, which application is incorporated herein by reference in its entirety.

FIELD OF THE INVENTION

The present invention relates to systems and methods for inserting a medical device into the brain for deep brain stimulation.

BACKGROUND OF THE INVENTION

Deep brain stimulation (DBS) and other related procedures involving implantation of leads and catheters are increasingly used to treat Parkinson's disease, dystonia, essential tremor, seizure disorders, obesity, depression, restoration of motor control, and other debilitating diseases. During these procedures, a catheter, lead, or other medical device is strategically placed at a target site in the brain. Locating the "best" target for stimulation in the brain can be a painstaking procedure.

Implantation of a lead for DBS generally involves the following preliminary steps: (a) anatomical mapping and (b) physiological mapping. Anatomical mapping involves mapping segments of an individual's brain anatomy using non-invasive imaging techniques, such as magnetic resonance imaging (MRI) and computed axial tomography (CAT) scans. Physiological mapping involves localizing the brain site to be stimulated. Step (b) can be further divided into: (i) preliminarily identifying a promising brain site by recording individual cell activity with a microelectrode and (ii) confirming physiological stimulation efficacy of that site by performing a test stimulation with a macroelectrode or microelectrode, however a macroelectrode is preferred.

Microelectrode recording is generally performed with a small diameter electrode with a relatively small surface area optimal for recording single cell activity. The microelectrode may be essentially a wire which has at least the distal portion uninsulated to receive electrical signals. The rest of the body or wire of the microelectrode may be insulated. The microelectrode functions as a probe to locate a promising brain site. Since a number of attempts may be required to locate the precise target site, it is desirable that the microelectrode be as small as possible to minimize trauma when the microelectrode is placed into the brain, in some cases, multiple times.

Once a brain site has been identified, a macroelectrode is used to test that the applied stimulation has the intended therapeutic effect. Once macrostimulation confirms that stimulation at the brain site provides the intended therapeutic effect, the macroelectrode is withdrawn from the brain and a DBS lead is permanently implanted at the exact site.

A conventional procedure for carrying out the microelectrode recording phase of DBS may involve the following detailed steps: (1) placing a stereotactic frame on the subject, which stereotactic frame is a device temporarily mounted on the head to assist in guiding the lead system into the brain; (2) performing MRI or equivalent imaging of the subject with the stereotactic frame; (3) identifying a theoretical target using a planning software; (4) placing the subject with the stereotactic frame in a head rest; (5) using scalp clips, cutting the subject's skin flap in the head, exposing the working surface area of the cranium; (6) placing the stereotactic arc with target coordinate settings and identifying the location on the skull for creation of a burr hole; (7) removing the arc and drilling a burr hole in the patient's skull; (8) placing the base of the lead anchor; and (9) with the microelectrode recording drive attached, and with an appropriate stereotactic frame adaptor inserted into the instrument guide, placing the stereotactic arc.

Next, (10) advancing a microelectrode cannula (or several at a time) and an insertion rod into the brain until they are approximately 25-35 mm above the target; (11) removing the insertion rod, and leaving the cannula in place; (12) inserting a recording microelectrode such that the tip of the microelectrode is flush with the tip of the microelectrode cannula; (13) connecting the connector pin of the recording microelectrode to a microelectrode recording system; (14) starting approximately 25 mm above the target, advancing the microelectrode into a recording tract at the specified rate using the microdrive; and (15) if the target is identified, removing the recording microelectrode cannula and recording microelectrode and leaving a stimulation or recording lead or similar device in their place.

Some physicians might use additional steps, fewer steps, or perform the steps in a different order.

On average, a single microelectrode recording tract takes approximately 30 minutes to perform. Each microelectrode recording tract requires placement of a larger diameter insertion cannula at a distance of 25-35 mm above the target site through viable brain tissue. Each time an object is inserted into the brain there is approximately a 5% risk of hemorrhage. Creating multiple tracts increases the risk for intracranial bleeding, duration of operation, post-operative infection, and operative risk. Creating new tracts is fraught with misalignment/misplacement problems because the introduction cannulas may not trace the exact pathways desired.

There is, therefore, a need to provide a system and method for implanting a medical device such as a lead into the brain that reduces the duration of the operation, reduces the number of repetitive invasive tracts created to find the "best" target site, reduces post-operative infection, and reduces operative risk to provide optimal physiological therapy.

SUMMARY OF THE INVENTION

The present systems and methods address the above and other needs by providing systems and methods for implanting a medical device such as a lead into the brain and avoids lead displacement once the "best" target site in the brain is located and components such as a recording microelectrode and a cannula are removed from the stereotactic frame.

The present systems and methods include a slit cannula, an elongated medical device within the lumen of the slit cannula, and a lock for securing the elongated medical device through the slit in the cannula. The lock is fastened to a reference platform, which reference platform is attached to a stereotactic frame.

In one aspect of the present systems and methods, the elongated medical device is a lead or catheter with an offset portion. The offset portion may be a tab, knob, bulge, parallel lead, or any other structure along the side of the lead to which the lock may attach. The offset portion may also be a paddle electrode connector or other electrode connector of the lead. The electrode connector is capable of forming an electrical connection with an operating room cable connected to an external trial stimulator.

In another aspect of the present systems and methods, the elongated medical device has a lumen through its axis, and the lumen does not continue through the offset portion. The lumen of the lead may be dimensioned to permit a microelectrode to be inserted into the lead lumen.

Conventionally, when a cannula enveloping a lead is removed from a stereotactic frame, the cannula is pulled upward, away from the brain, as it slides like a sleeve off of the lead. Before the distal tip of the cannula exits the skull, the proximal tip of the cannula has covered the proximal end of the lead. Thus, as the proximal length of the lead is cloaked by the cannula and the distal length of the lead is cloaked by the skull, dura mater, and brain, no portion of the lead is visible to the surgeon. Yet in order to insure that the lead does not move during removal of the cannula and other structures, e.g., the recording microelectrode, it is critical that at least a portion of the lead be seen by the surgeon at all times, and if possible, locked into place. The present systems and methods avoid lead displacement by permitting a surgeon to view and lock the lead into place at all times during the removal of a cannula and other structures such as the recording microelectrode.

The present systems and methods allow a surgeon to remove a recording microelectrode before or after a cannula is removed. The present systems and methods also allow a surgeon to place a non-isodiametric lead within a cannula lumen. Further, the present systems and methods prevent fluid ingress into the connector end of a lead. Further still, the present systems and methods allow a surgeon to deliver continuous stimulation and receive continuous recording signals through the lad during removal of the surgical insertion tools (i.e., the cannula, recording microelectrode, and other devices) in order to continuously monitor any potential changes in stimulation efficacy of the lead during removal of the insertion tools.

BRIEF DESCRIPTION OF THE DRAWINGS

The above and other aspects of the present systems and methods will be more apparent from the following more particular description thereof, presented in conjunction with the following drawings wherein:

FIG. 4 shows a close-up, perspective view of the removal of the slit cannula from the offset lead/lead lock assembly of FIG. 1B;

FIG. 5 shows a top view of the lead, lead lock, and slit cannula of FIG. 1B.

Corresponding reference characters indicate corresponding components throughout the several views of the drawings.

DETAILED DESCRIPTION OF THE INVENTION

The following description includes the best mode presently contemplated for carrying out the present systems and methods. This description is not to be taken in a limiting sense, but is made merely for the purpose of describing the general principles of the present systems and methods. The scope of the invention should be determined with reference to the claims.

The systems and methods described herein that allow for visualization and locking of a deep brain stimulation (DBS) lead, or other elongated medical structure, during a surgical tool removal process of a DBS procedure, hence eliminating the risk of lead movement. Visualization and locking of the lead during the surgical removal process can be accomplished using a unique lead system.

For this disclosure, the lead system refers to (1) a lead, (2) a slit cannula, (3) a lead lock, and (4) a recording microelectrode or stylet. The lead may have a lumen for receiving the recording microelectrode. The lead is also dimensioned to fit within the lumen of the slit cannula. The lead lock is capable of attaching to the lead through the slit of the cannula. Alternatively, the lead has an offset portion that extends from the main body of the lead, through the slit cannula, to the lead lock. The lead lock is capable of attaching to the offset portion of the lead. The lead lock is, in turn, anchored to a stereotactic frame, or other permanent reference point.

Because the lead is anchored by means of a lead lock to a permanent reference point, a surgeon is able to remove both the slit cannula and the recording microelectrode without disturbing the location of the lead within the brain. Even a slight movement of a lead from its target site within the brain of a patient can dramatically decrease the therapeutic effect of the lead for the patient. Thus, the present systems and methods lock the lead into place once the lead has been placed in a location of maximum therapeutic effect for the patient.

Figure 1A:
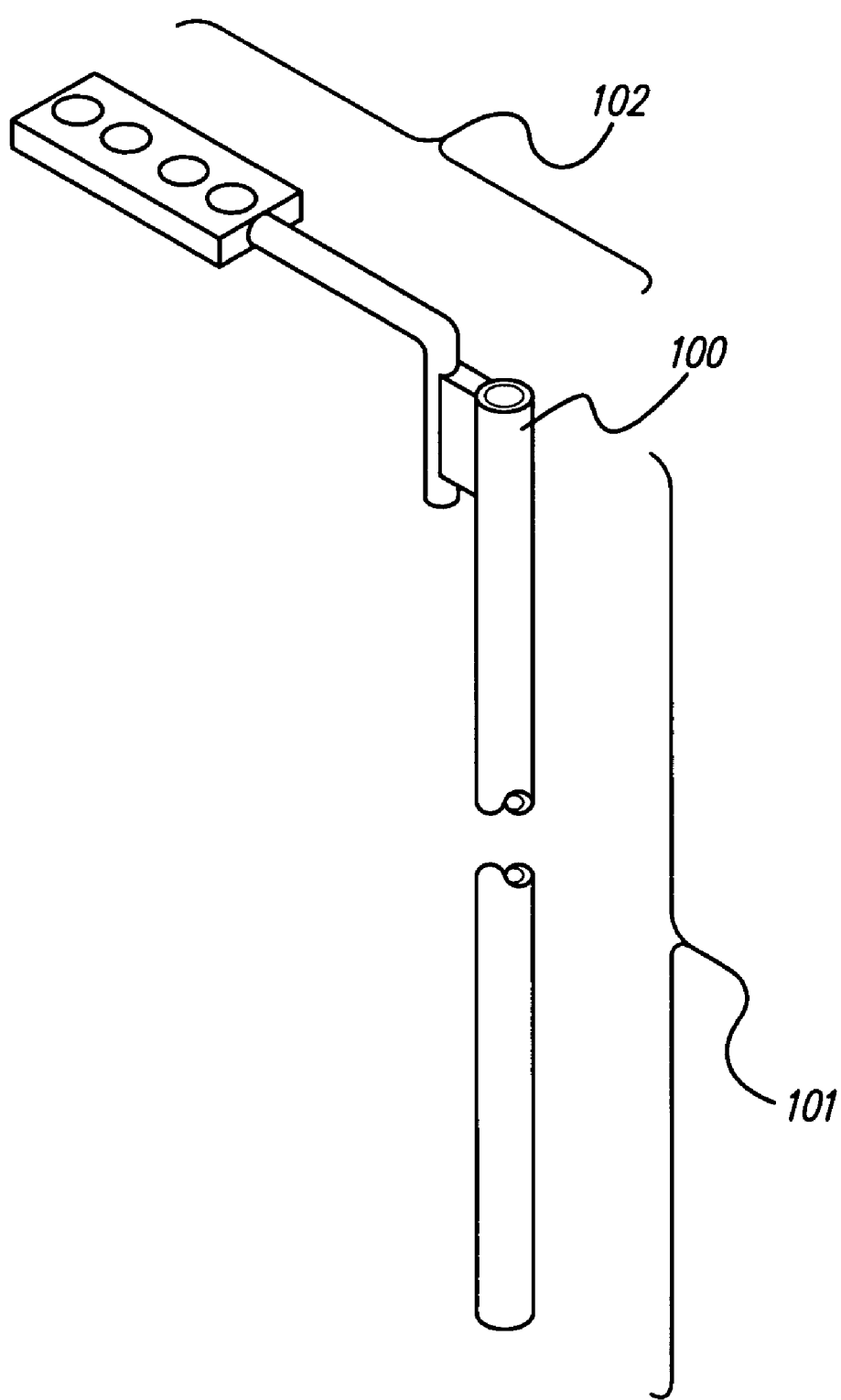
FIG. 1A shows a front view of an offset lead of the present systems and methods
Figure 1B:
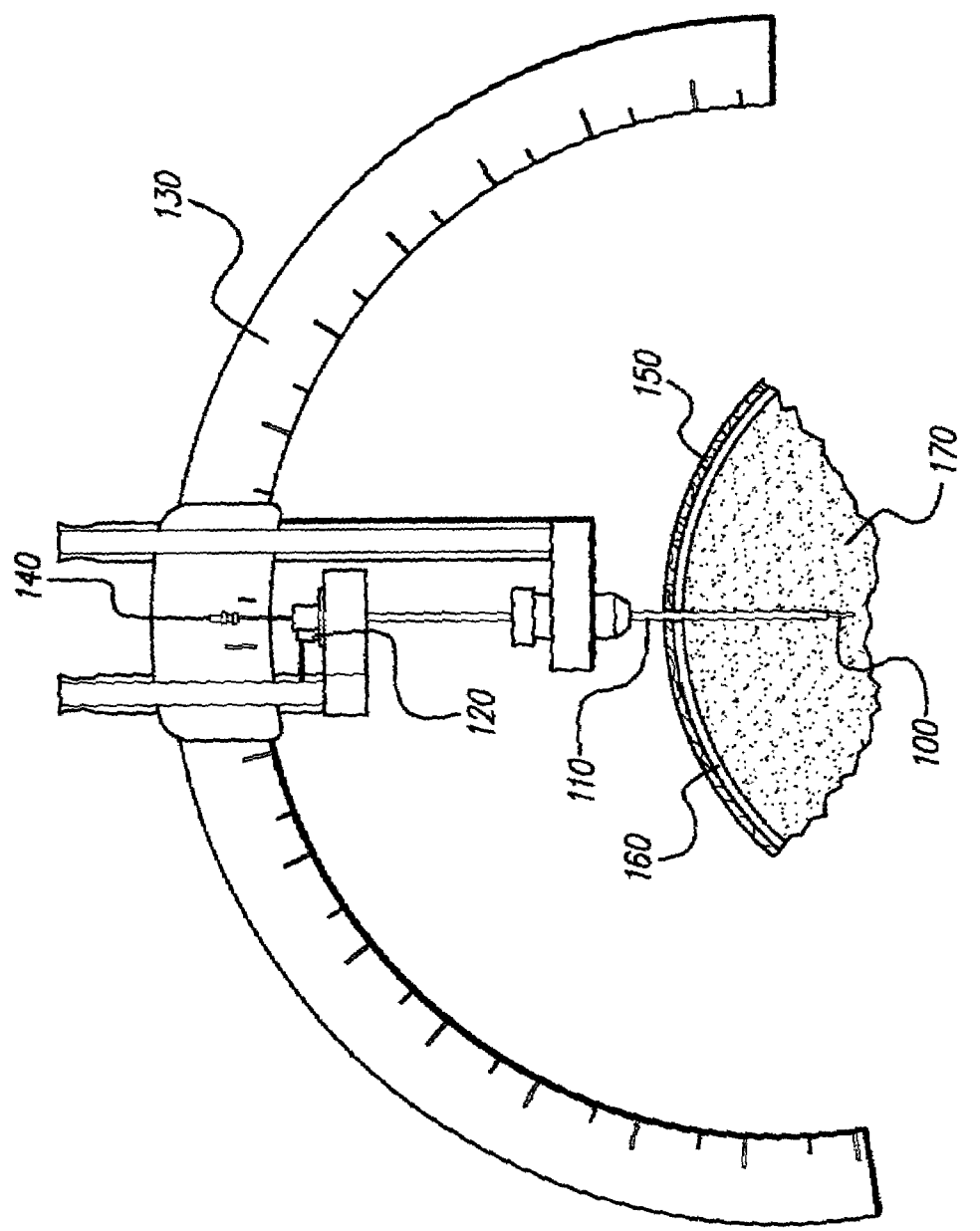
FIG. 1B shows a front view of a DBS lead system of the present systems and methods.

As shown in FIG. 1A, the lead may be an offset lead 100 with a lead body 101 and an offset portion 102. Referring to FIGS. 1A and 1B, lead body 101 fits within the lumen of a slit cannula 110 while offset portion 102 remains connected to lead body 101 through the slit of cannula 110. A lead lock 120 attaches to offset portion 102 of lead 100 and thereby anchors lead 100 through cannula 110 to a stereotactic frame 130.

FIG. 1B shows a front view of an embodiment of the DBS lead system of the present systems and methods. The DBS lead system of FIG. 1B includes offset lead 100, which can also be a catheter or other similar insertable medical device; slit cannula 110; and lead lock 120. FIG. 1B also shows stereotactic frame 130, which holds the components of the DBS lead system during a DBS procedure; a stylet and/or recording microelectrode 140 inserted within the lumen of lead 100; and a skull 150, dura mater 160, and brain 170 of a patient. The DBS lead system is fully engaged with stereotactic frame 130, and the distal ends of both offset lead 100 and slit cannula 110 are inserted into brain 170.

Figure 2A:
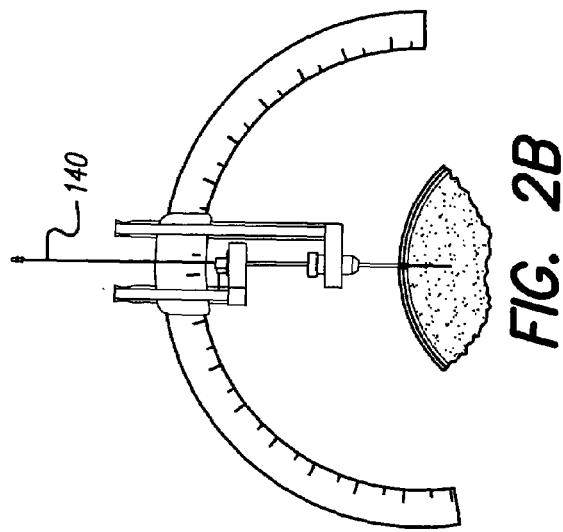
FIGS. 2A-2D represent front views of the DBS system showing a sequence for removal of the surgical insertion tools of FIG. 1B.
Figure 2B:
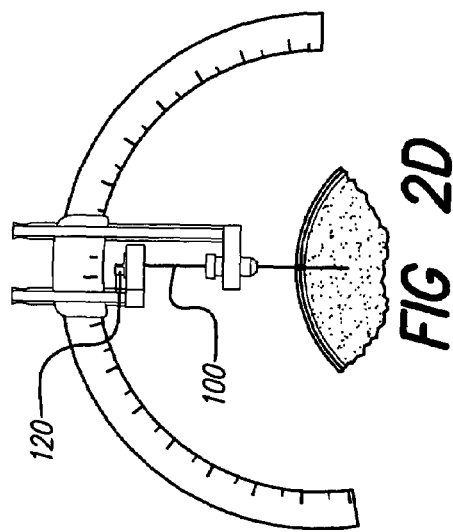
Figure 2C:
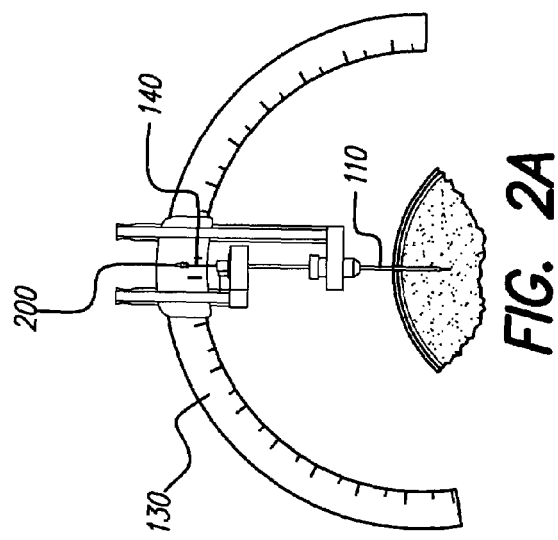
Figure 2D:
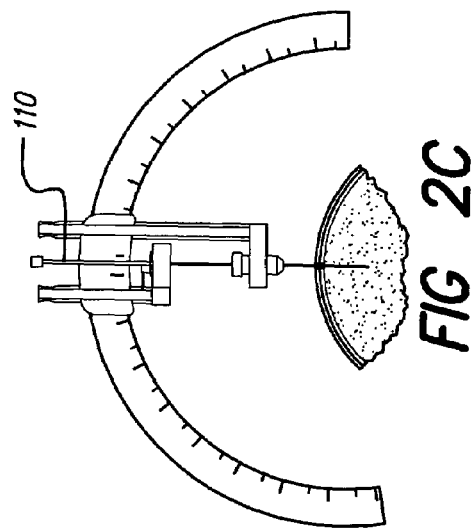

FIGS. 2A-2D illustrate the procedure used to remove microelectrode 140 and/or cannula 110 of the DBS lead system shown in FIG. 1B. FIG. 2A shows the DBS lead system in stereotactic frame 130 with microelectrode 140 and with slit cannula 110 fully inserted. FIG. 2B depicts the removal of microelectrode 140 from the DBS lead system. FIG. 2C depicts the removal of cannula 110 from the DBS lead system. The steps of removing microelectrode 140 and cannula 110 can be performed in reverse order when the proximal end of microelectrode 140 is moved or bent to the side, through the slit of cannula 110, and cannula 110 is removed. Cannula 110 has a slit 400 (shown in FIG. 4) along its entire length that, inter alia, permits the body of microelectrode 140 to be moved or bent to the side, i.e., outside the lumen of cannula 110, in order for cannula 110 to be removed. If connector 200 (see FIG. 2A), at the proximal end of microelectrode 140, has an outer diameter less than the inner diameter of slit cannula 110, no movement of microelectrode 140 is required. FIG. 2D depicts the removal of all the insertion tools of the DBS lead system, thus leaving offset lead 100 securely locked into place by lead lock 120.

FIGS. 1B through 2D show lead 100 locked to lead lock 120 at an elevated point above the skull of a patient. However, the present systems and methods include invention locking lead 100 to lead lock 120 at locations along lead 100 that are closer to the skull than shown in FIGS. 1B through 2D. In some examples, lead 100 is locked to lead lock 120 just above the site of entry into the skull. Lead 100, or another elongated medical device locked by lead lock 120, may be made of malleable or elastic material. Therefore, lead 100 may move slightly when other devices in contact with lead 100 are moved. Lead 100 may move despite the fact that it is locked into place by icad lock 120. Locking the lead 100 at or just above the site of entry into the skull minimizes unwanted movement of lead 100 during movement of other structures in contact with lead 100. Movement is minimized because lead 100 is stabilized by lead lock 120, the skull, and brain tissue and because the distance between the point at which lead 100 is locked and the target site in the brain is minimized.

Figure 3:
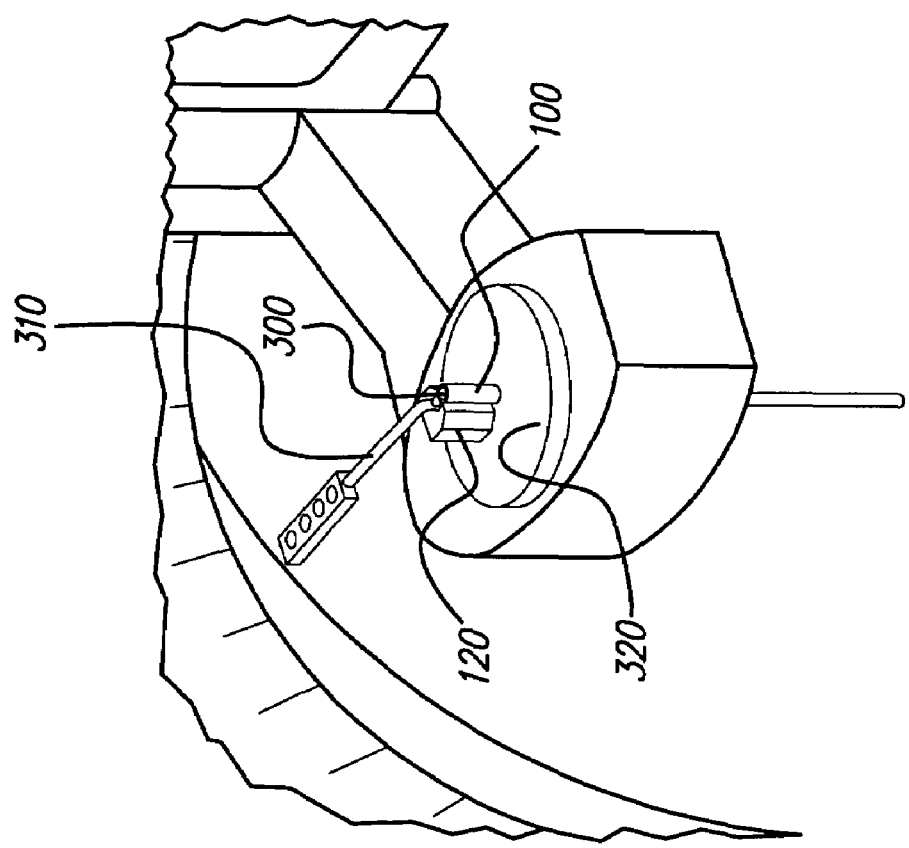
FIG. 3 shows a perspective view of the lead and lead lock of the DBS lead system shown in FIG. 1B.

FIG. 3 is a perspective view of offset lead 100 and lead lock 120 of the DBS lead system shown in FIG. 1B. In this embodiment of the offset lead, the proximal end of offset lead 100 has a lumen 300 terminating at approximately the same height as an arm 310 of the offset portion 102 of offset lead 100. Lead lock 120 is attached to an insertion tool holder 320. Lead lock 120 clamps a base 600 (see FIG. 6) of offset portion 102 of offset lead 100 securely into place. In an alternate embodiment, lead lock 120 may secure offset lead 100 through a spring-loaded clamp, vice, or similar mechanism capable of securing offset lead 100. In yet another alternate embodiment, offset lead 100 may have a tab, knob, bulge, or any other structure to which lead lock 120 may attach instead of base 600 (see FIG. 6) of offset portion 102.

Offset lead 100 is described as non-isodiametric because its diameter changes due to an attachable structure along its length. However, in yet another embodiment of the present system, an isodiametric lead, i.e., a lead with no attachable structures along its length, may also be attached to or secured by an embodiment of lead lock 120. For example, a lead could be pinched by prongs, pierced by hooks or pins, sutured by a pin and thread, or otherwise restrained by a break through a slit 400 (see FIG. 4) of cannula 110. In some examples, a lead or elongated medical device is secured through the slit 400 (see FIG. 4) in cannula 110 by a structure that may be fastened to the stereotactic frame or a similar reference platform in the case that the surgery is performed without a stereotactic frame.

FIG. 4 is a close-up, perspective view of the removal of the slit cannula from the lead/lead lock assembly of FIG. 1B. The slit 400 of cannula 110 allows for use of an isodiametric or non-isodiametric lead 100. This allows for use of a lead that has a highly reliable connector such as a silicone paddle 410, or other paddle electrode connector with electrical contacts 420. Silicone paddle 410 is capable of being connected to an external trial stimulator via an operating room cable. Silicone paddle 410 forms a silicone to silicone seal between the electrical contacts 420 at the coupling of a lead and an implantable pulse generator.

Because silicone paddle 410 is adjacent to the main portion of offset lead 100, lumen 300 (see FIG. 3) of offset lead 100 does not extend into the arm 310 of offset portion 102 of offset lead 100. Therefore, it is impossible for fluid to travel through lumen 300 (see FIG. 3) to the implantable pulse generator. Conventionally, unwanted fluid penetration via the lead to an implantable pulse generator is possible, for example, with an isodiametric lead and use of connectors such as those available from Bal Seal Engineering of Foothill Ranch, California. At the coupling of a Bal Seal, a series of circular springs surround the circumference of the lead contacts and are longitudinally spaced by polyurethane, silicone, or epoxy seals. In order for the lead to couple with the implantable pulse generator, the lead contacts must pass each consecutive seal, thereby disturbing the original structure of the spacer seals and compromising the ability of the Bal Seal to prevent fluid penetration. As mentioned earlier, fluid penetration using an offset lead 100 is impossible as lumen 300 (see FIG. 3) does not travel to silicon paddle 410, which paddle 410 is used to electrically connect to an implantable pulse generator. In an alternate embodiment, offset lead 100 without paddle 410 could be coupled with a Bal Seal connection mechanism, or any other functional connection mechanism, and fluid ingress would still be avoided as lumen 300 (see FIG. 3) does not travel to the site of connection in non-isodiametric offset lead 100.

In summary, the offset feature of offset lead 100 prevents fluid ingress through a paddle, Bal Seal, or other connection mechanism. As shown in the embodiment in FIG. 4, because offset lead 100 has an offset portion 102, paddle 410 may be used, thereby providing a superior sealing mechanism, especially as compared to the Bal Seal mechanism.

Slit 400 along the entire length of cannula 110 also allows the physician to visualize the offset lead 100 during removal of cannula 110. Another advantage of slit cannula 110 is that the stylet or microelectrode 140 (see FIG. 1B) can be removed before or after cannula 110 is removed.

FIG. 5 is a top view of the offset lead 100, lead lock 120, and slit cannula 110 of FIG. 1B. Arm 310, silicone paddle 410 with electrical contacts 420, and insertion tool holder 320 are also shown.

Figure 6:
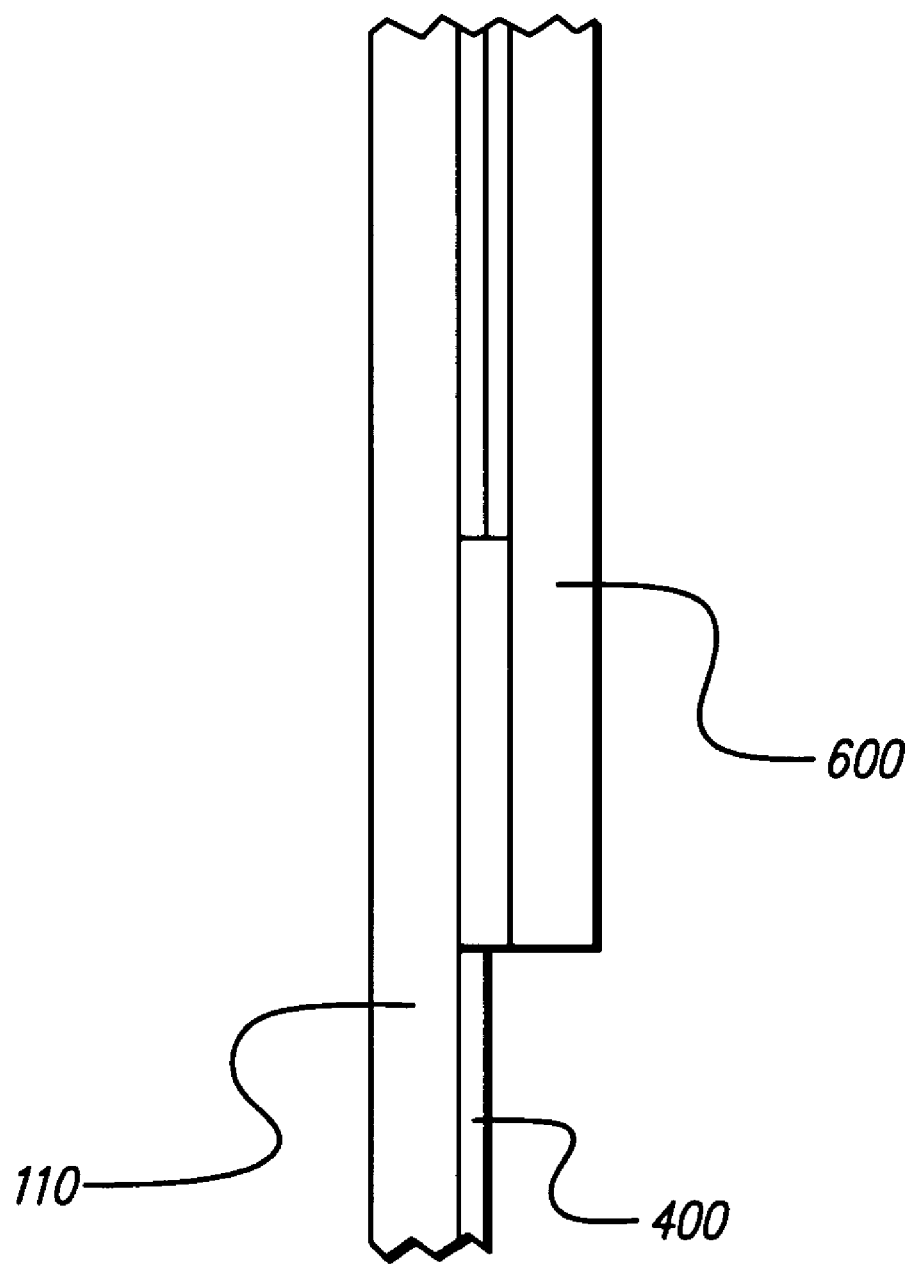
FIG. 6 shows a close-up, side view of the slit cannula and the base of the offset portion of the lead of FIG. 4.

FIG. 6 is a close-up, side view of slit cannula 110 with slit 400 and base 600 of offset portion 102 of lead 100 of FIG. 4. As previously mentioned, base 600 of offset portion 102 holds lead 100 (referring to FIGS. 1A and 1B) stable while the temporary surgical tools are removed. When cannula 110 and microelectrode 140 are removed, a lead anchor lock or burr hole plug can be engaged to lock lead 100 in place, at which time lead lock 120 can safely be disengaged. Then, stereotactic frame 130 (shown in FIG. 1B) can be removed without disturbing lead 100. The stereotactic frame adapters may consist of two halves that facilitate easy removal of the frame without disturbing the position of lead 100. Referring to FIG. 4, lead lock 120 permits silicone paddle 410 to attach to an external trial stimulator via an operating room cable such that clinical efficacy, i.e., physiological response stimulation via lead 100, can be observed during the removal of the recording microelectrode 140 and insertion cannula 110. Thus, a change in clinical response to stimulation will immediately be observed and adjustments during the removal process can be made.

While the systems and methods herein disclosed have been described by means of specific embodiments and applications thereof, numerous modifications and variations could be made thereto by those skilled in the art without departing from the scope of the invention set forth in the claims.

What is claimed is:

1. A deep brain stimulation system comprising:

a cannula having a lumen and a slit, the slit extending through a portion of a length of the cannula;

an elongated medical device dimensioned to be insertable within the cannula lumen, the medical device comprising an offset portion that extends laterally out of the cannula through the slit when the medical device is inserted in the lumen;

a reference platform for supporting the medical device; and a lock for releasably securing the offset portion of the elongated medical device to the reference platform, the lock engaging the offset portion which extends through the cannula slit;

wherein the elongated medical device includes a lumen along its length, wherein the lumen of the elongated medical device does not extend through the offset portion.

2. The system of claim 1, further comprising a stereotactic frame, wherein the reference platform is attached to the stereotactic frame.

3. The system of claim 1, wherein the lock, when engaged, is configured to prevent further passage of the elongated medical device through the lumen.

4. A deep brain stimulation system comprising:
a cannula having a lumen and a slit, the slit extending through a portion of a length of the cannula;
a medical device dimensioned to be insertable within the lumen of the cannula and comprising an offset portion that extends laterally out of the cannula through the slit when the medical device is inserted in the lumen; and
a reference platform for supporting at least a portion of the medical device;
wherein the medical device further comprises a lumen along its length that does not extend through the offset portion.

5. The system of claim 4, further comprising a lock for releasably securing the offset portion of the medical device to the reference platform.

6. The system of claim 4, wherein the offset portion further comprises a paddle electrode connector.

7. The system of claim 6, wherein the paddle electrode connector is configured to form an electrical connection with an operating room cable, wherein the cable is configured to connect to an external trial stimulator.

8. A deep brain stimulation system comprising:
a cannula having a lumen therein for passage of a medical device into a patient and a slit, the slit extending through a portion of a length of the cannula, the medical device comprising an offset portion that extends laterally out of the cannula through the slit when the medical device is inserted in the lumen;
a reference platform for supporting the medical device; and
a lock for releasably securing the offset portion of the medical device to the reference platform, the lock engaging the offset portion which extends through the cannula slit;
wherein the medical device includes a lumen that does not extend through the offset portion.

9. The system of claim 8, wherein said medical device comprises at least one or more of a lead, a catheter, a microelectrode, and a stylet.

10. The system of claim 8, wherein said medical device includes a lumen and wherein said system further comprises a microelectrode dimensioned to be insertable into the lumen of the medical device.

11. The system of claim 8, wherein said cannula is removeably coupled to said reference platform.

12. A deep brain stimulation system comprising:
a cannula having a lumen therein for passage of a medical device into a patient and a slit, the slit extending through a portion of a length of the cannula, the medical device comprising an offset portion that extends laterally out of the cannula through the slit when the medical device is inserted in the lumen;
a reference platform for supporting the medical device; and
a lock for releasably securing the offset portion of the medical device to the reference platform, the lock engaging the offset portion which extends through the cannula slit;
wherein the cannula is configured to be removable from the medical device and the lock without disturbing the position of the medical device.

13. The system of claim 12, further comprising a stereotactic frame, wherein the reference platform is attached to the stereotactic frame.

14. A method for securing a lead in a deep brain stimulation system comprising the steps of:
providing a cannula with a lumen and a slit, the slit extending through a portion of a length of the cannula;
inserting a lead into the lumen of the cannula, the lead having an offset portion that extends laterally out of the cannula through the slit when the lead is inserted in the lumen and that includes an electrode connector;
releasably securing the offset portion of the lead to the reference platform through the slit using a lead lock; and
fastening the lead lock to a reference platform of a stereotactic frame.

15. A method for securing a lead in a deep brain stimulation system comprising the steps of:
providing a cannula with a lumen and a slit, the slit extending through a portion of a length of the cannula;
inserting a lead into the lumen of the cannula, the lead having an offset portion that extends laterally out of the cannula through the slit when the lead is inserted in the lumen; and
releasably securing the offset portion of the lead to the reference platform through the slit;
wherein the lead further includes a lumen along its length that does not extend through the offset portion.

16. The method of claim 15, wherein the step of releasably securing the offset portion of the lead further comprises using a lead lock to secure the offset portion of the lead to the reference platform through the slit.

17. The method of claim 16, wherein the step of releasably securing the offset portion of the lead further comprises pinching the lead with the lead lock.

18. The method of claim 16, wherein the step of releasably securing the offset portion of the lead further comprises suturing the lead to the lead lock.

19. The method of claim 16, wherein the step of releasably securing the offset portion of the lead further comprises piercing the lead with the lead lock.

20. The method of claim 16, wherein the step of releasably securing the offset portion of the lead further comprises clamping the lead lock to the lead.

\* \* \* \* \*